United States Patent [19]

Suga et al.

[11] Patent Number: 4,568,683

[45] Date of Patent: Feb. 4, 1986

[54] LIPID METABOLISM WITH PANTETHEINE-S-SULFONIC ACID

[75] Inventors: Tetsuya Suga, Tokyo; Omanabu Katsumata, Kanagawa; Tomoyasu Tashiro, Tokyo, all of Japan

[73] Assignee: Sogo Pharmaceutical Company Limited, Sagamihara, Japan

[21] Appl. No.: 598,238

[22] Filed: Apr. 9, 1984

Related U.S. Application Data

[63] Continuation-in-part of Ser. No. 443,066, Nov. 19, 1982, abandoned.

[30] Foreign Application Priority Data

Dec. 4, 1981 [JP] Japan ................................ 56-194392
Mar. 30, 1982 [JP] Japan ................................ 57-50167

[51] Int. Cl.[4] ................ A61K 31/205; A61K 31/185; A61K 31/44
[52] U.S. Cl. .................................... 514/358; 514/554; 514/578; 260/501.12; 260/513 N

[58] Field of Search ................ 424/315, 263, 316; 514/554, 578, 358

[56] References Cited

PUBLICATIONS

Moiseenok, A., et al., *Khim.-Farm. Zh.*, 1981, 15(6), 76–81.
*Chemical Abstracts*, 90:37873w (1979) [Kopelevich, V., et al., *Khim.-Farm. Zh.*, 1978, 12(8), 72–6].

*Primary Examiner*—Richard A. Schwartz
*Attorney, Agent, or Firm*—Browdy and Neimark

[57] ABSTRACT

A lipid metabolism improving drug or pharmaceutical composition contains pantetheine-S-sulfonic acid as an active ingredient. When an effective dose of pantetheine-S-sulfonic acid or a pharmaceutically active, non-toxic salt thereof is administered to an animal, such as a human, in pure form or composition form, the lipid concentration in the plasma is lowered, lipid peroxide concentration in the serum and liver is lowered, B-lipo protein-cholesterol concentration in serum is decreased and HDL-cholesterol concentration is increased.

9 Claims, No Drawings

LIPID METABOLISM WITH PANTETHEINE-S-SULFONIC ACID

This is a continuation-in-part of parent application Ser. No. 443,066, filed Nov. 19, 1982, now abandoned, the contents of which are hereby incorporated by reference.

The present invention relates to the improvement of lipid metabolism. It more particularly relates to a lipid metabolism improving composition comprising pantetheine-S-sulfonic acid or a salt thereof as an active ingredient, and to the use of said pantetheine-S-sulfonic acid or salt to bring about improved lipid metabolism.

The inventors noticed a physiological activity of a sulfonic acid group in vivo and, after intensive investigations of sulfonic acid group-containing compounds, we have found that pantetheine-S-sulfonic acid extracted from natural materials has a plasma lipid lowering and a preventive effect in Triton-hyperlipidemic animals and that they have also effects of lowering the lipid peroxide concentration in serum and liver which is raised by liver injury due to organic solvents and furthermore lowering the β-lipoprotein-cholesterol content and increasing HDL-cholesterol levels in serum. The present invention has been completed on the basis of these findings.

Pantetheine-S-sulfonic acid, which is the active ingredient of the present invention, is a known compound represented by the following formula [I]:

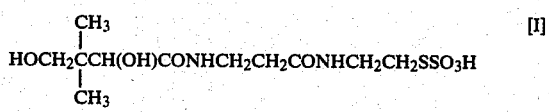

This compound is extracted from carrots [Chem. Pharm. Bull. Vol. 22 (7), 1632–1638 (1974)]. This is a safe, natural compound having no toxicity. Recently, it has become possible to produce this compound from D-pantothenic acid and 2-aminoethanethiolsulfuric acid in an industrially advantageous manner. A process for the production thereof with a satisfactory purity in a high yield has been developed (Japanese Patent Laid-Open No. 39061/1981). It has been proved that this compound acts as a precursor of coenzyme A in vivo [Japan. J. Microbiol., Vol. 16 (3), 239–242, 1972].

U.S. Pat. Nos. 3,803,119 and 3,876,799 of Tamura et al disclose the feeding of this compound to unweaned infants to promote the growth of lactobacillus bifidus in their intestines to improve digestion of milk; this bacteria is only found in the intestines of infants, and such use has no utility for adults. This compound has also been injected into rats with vitamin $B_3$ deficiency, where it was found to elevate the contents of pantethenic co-enzymes (Kopelevich et al, Chemical Abstracts 90:37873W).

However, it has not previously been known that this compound has lipid metabolism improving effects such as a serum lipid concentration lowering effect. In patients with hepatic injury, glutamic oxaloacetic transaminase (GOT) and glutamic pyruvic transaminase (GPT) are increased generally. And in patients with liver troubles due to cholangia, alkaline phosphatase activity is increased.

Further, it has been known that organic solvents peroxidize a membrane lipid of liver microsome to form a peroxide [Exp. Mol. Path. 12:224, (1970)]. It is known that the lipid peroxide thus formed causes the following various problems. Furthermore, it is said that the lipid peroxide is related in some way to carcinogenesis.

(1) If lipid peroxide is formed in cells, it damages cell membranes or denatures enzyme protein to cause acute, local disorders in the tissue.
(2) If a large amount of lipid peroxide is released from the cells, serum lipid peroxide is increased to cause serum hyperlipoperoxidemia, whereby disorders of peripheral organs are invited.
(3) Fluorescent substances such as ripofuscin (which is essentially a complex of lipid peroxide and protein) are stored chronically in cells and participate in the aging process of the cells.
(4) Lipid peroxide invites the agglutination of blood platelets and contraction of the blood vessels due to prostaglandin formation in the blood platelets.

Thus, it is clinically quite significant to control lipid peroxide having the above-mentioned harmful effects and the development of drugs for controlling lipid peroxide has eagerly been demanded in the art.

The inventors investigated the mechanism of lipoperoxides formation caused by liver disorders for the purpose of developing a drug for curing or preventing unusual lipid metabolism according to hepatic injury. The inventors supposed the following mechanism: in the course of the formation of lipid peroxide, hydrogen is first taken out of the methylene group interposed between the double bonds in an unsaturated fatty acid to form a radical, and then it is reacted with oxygen to form a peroxy radical, which attacks other active methylene groups and which per se is converted into a hydroperoxide. These active methylene groups are further converted into a radical by the reaction with other active methylene groups. Thus, a series of chain reactions is initiated. The lipid peroxide is formed in the form of a hydroperoxide successively and oxygen is consumed. In patients with hepatic injury, the lipid peroxide is increased and SH functions are deteriorated. Intensive investigations were made on various compounds from these viewpoints.

As a result, it was found that among numerous compounds, pantetheine-S-sulfonic acid is particularly converted into pantetheine or coenzyme A which is a compound containing a SH group in vivo. The inventors considered that this compound could complement the deterioration of SH functions. The inventors considered also that a radical formed in the course of the lipid peroxide formation can be released from the above chain reaction system by $SO_3^{2-}$ ion liberated when pantetheine-S-sulfonic acid is converted into pantetheine, whereby the lipid peroxide formation can be controlled. After further investigations made on the basis of these inferences, the inventors have confirmed that pantetheine-S-sulfonic acid is effective for the treatment of hyperlipidemic patients and abnormal lipid metabolism observed in patients with liver disorders, since pantetheine-S-sulfonic acid lowers lipid peroxide concentrations in serum and liver.

Further, the inventors have found that pantetheine-S-sulfonic acid has quite specific, selective physiological effects in that it decreases β-lipoproteincholesterol but increases HDL-cholesterol in normolipidemic animals, whereby it exhibits an excellent antiatherosclerotic activity.

As will be shown in tests given below, pantetheine-S-sulfonic acid has a quite excellent lipid metabolism-improving effect. Particularly, it lowers the plasma lipid content and prevents liver disorders and cholangia, whereby lipid peroxide concentrations in the serum and liver are lowered. Furthermore, as a result of lowering of the serum β-lipoprotein-cholesterol content and increasing serum HDL-cholesterol, atherosclerosis can be prevented.

In addition, pantetheine-S-sulfonic acid has no problem of safety or toxicity, since it is a natural product extracted from carrots. In toxicity tests carried out by using rats, it had an $LD_{50}$ of at least 10 g/kg in the oral administration. This fact means that said compound is substantially non-toxic. In addition, pantetheine-S-sulfonic acid can be handled easily and preparations containing the same can be produced easily. Thus, this compound is quite suitable for use as a material for a medicine in all aspects.

In the present invention, not only the free acid of formula [I] but also its salts can be used as the active ingredient. As the salts, there may be mentioned organic salts such as the pyridinium salt and amine salts, and inorganic salts such as alkali metal salts, especially the sodium and potassium salts, and alkaline earth metal salts, especially the magnesium and calcium salts. Among them, the alkali metal salts and alkaline earth metal salts are preferred and calcium salt is particularly preferred.

As for analogous compounds of pantetheine-S-sulfonic acid, pantethine has been known. However, this compound is an amorphous, viscous substance which is inconvenient for handling. If pantethine is administered perorally, it tastes extremely bitter. On the other hand, pantetheine-S-sulfonic acid is a white, fine crystalline substance having substantially no bitter taste. As compared with pantethine, pantetheine-S-sulfonic acid has a significant serum lipid peroxide formation controlling effect.

The lipid metabolism improving pharmaceutical composition of the present invention may be administered either orally or externally. In oral administration, it may be used in the form of soft or hard capsules, tablets, granules, fine granules or powders. In the external administration, it may be used in the form of injections, intravenous drips and, in some cases, suppositories.

The dose of the active ingredient of the present invention, which varies depending on the symptoms and the form of a drug, is suitably 100 mg/day to 10 g/day, for example 300–6,000 mg/day particularly 500 to 3000 mg/day in the treatment of human bodies.

In producing the preparations containing the active ingredient of the present invention, a surfactant, excipient, lubricant, corrigent, colorant, flavor, preservative, suspending agent, wetting agent, film-forming agent, coating aid and other adjuvants may be used properly.

A method of tests for confirming the effect of the above-mentioned compound [I] in improving the lipid metabolism will be shown below.

TEST 1

Male Wistar-Imamichi rats weighing about 180 g obtained from JCL Co., Ltd. were used. The rats were divided into 6 groups, i.e., a control group (normal models), a Triton-control group (hyperlipidemic models), a Triton-pantethine simultaneous administration group, a Triton-pantetheine-S-sulfonic acid simultaneous administration group, a Triton-pantethine pretreatment group and a Triton-pantetheine-S-sulfonic acid pretreatment group. Each group comprised 10 rats. The animals were fed with a commercially available type CE-2 diet (JCL Co., Ltd.) and water ad libitum. The drugs were dissolved in saline at a rate of 200 mg/ml and Triton WR-1339 was dissolved in saline at a rate of 100 mg/ml.

5 ml/kg of saline was given orally to the rats of the control group once a day at 11 A.M. for one week. The fasting was continued for 6 h after the final treatment. Then, 5 ml of blood was taken from the heart by cardiac puncture under ether anesthesia and plasma lipids were determined by conventional methods. In the Triton-control group, 5 ml/kg of saline was given orally to the rats once a day at 11 A.M. for one week. In the final administration, 400 mg/kg of Triton WR-1339 was injected into rats through a common jugular vein. After the injection, the fasting was started. After 6 h, 5 ml of blood was taken from the heart by the method of cardiac puncture under ether anesthesia and plasma lipids were determined by conventional methods. In Triton-pantethine simultaneous administration group, rats were given orally 1000 mg/kg of pantethine solution once a day at 11 A.M. and simultaneously 400 mg/kg of Triton WR-1339 was injected into rats through a common jugular vein. After Triton injection, the fasting was initiated. After 6 h, 5 ml of blood was taken from the heart by cardiac puncture under ether anesthesia and plasma lipids were determined by conventional methods. In Triton pantetheine-S-sulfonic acid simultaneous treated group, 1000 mg/kg of pantetheine-S-sulfonic acid solution was dosed orally to the rats once a day at 11 A.M. and simultaneously 400 mg/kg of Triton WR-1339 was injected into animals through a common jugular vein. After Triton injection, the fasting was continued 6 h and then 5 ml of blood was taken from the heart by cardiac puncture under ether anesthesia and plasma lipids were determined by conventional methods. 1000 mg/kg of pantethine solution was given orally to the rats of the Triton-pantethine pretreatment group once a day at 11 A.M. for one week. At the same time of final drug treatment, 400 mg/kg of Triton WR-1339 was injected into rats through a common jugular vein. After the injection, the fasting was initiated. 6 h later, 5 ml of blood was taken from the heart by cardiac puncture under ether anesthesia and plasma lipids were determined by conventional methods.

1000 mg/kg of pantetheine-S-sulfonic acid solution was given orally to the rats of the Triton-pantetheine-S-sulfonic acid pretreatment group once a day at 11 A.M. for one week. At the time of final drug treatment, 400 mg/kg of Triton WR-1339 was simultaneously injected through a common jugular vein. After the injection, the fasting was continued 6 h and then 5 ml of blood was taken from the heart by cardiac puncture under ether anesthesia and plasma lipids were determined by conventional methods. The methods of the determination of plasma lipids were as shown below. Pantetheine-S-sulfonic acid was used in the form of its calcium salt in all cases.

Triglyceride: Enzymic method (Triglyceride-G Test Wako)

Cholestrol: Enzymic method (Cholesterol-C Test Wako)

The results are shown in Table 1.

TABLE 1

Effects of Pantethine and Pantetheine-S—sulfonic acid on plasma lipids in Triton-hyperlipidemic rats

| Sample | Dose (mg/kg) | Plasma lipids (mg/dl) Cholesterol | Triglyceride |
|---|---|---|---|
| Control group | — | 70.8 ± 3.7 | 80.1 ± 5.6 |
| Triton-control group | — | 191.1 ± 7.0 | 2400.2 ± 225.5 |
| Triton-pantethine simultaneous treatment group | 1,000 | 149.5 ± 11.3° (21.8%) | 1726.5 ± 162.2° (28.1%) |
| Triton-pantetheine-S—sulfonic acid simultaneous treatment group | 1,000 | 166.7 ± 7.7° (12.8%) | 1647.8 ± 257.1* (31.3%) |
| Triton-pantethine pretreatment group | 1,000 × 7 | 153.3 ± 6.6* (19.8%) | 1772.0 ± 106.7° (26.2%) |
| Triton-pantetheine-S—sulfonic acid pretreatment group | 1,000 × 7 | 158.8 ± 7.6° (16.9%) | 1579.8 ± 207.7° (34.2%) |

*P < 0.1
°P < 0.05
*P < 0.01

Percentages in the parentheses indicate reduction rates based on the plasma lipids in the rats of the Triton-control group.

In Triton-control group, as compared with the control group, plasma cholesterol and triglyceride were increased significantly (P<0.001). This fact means that models of hyperlipidemic animals were obtained. Pantetheine-S-sulfonic acid exhibits an effect of reducing cholesterol equivalent to that of pantethine and also an effect of significantly reducing the triglyceride content. As compared with the group to which the drug was given only once, the pretreated group showed slightly lower cholesterol and triglyceride values. It was thus proved that pantetheine-S-sulfonic acid has an effect of preventing the increase of plasma lipid concentration caused by Triton.

In the tests, the pantethine-pretreated group had symptoms of serious diarrhea (9 rats in the 10-membered group had symptoms of diarrhea and one of them died on the 6th day of the treatment). On the other hand, only one rat in the 10-membered pantetheine-S-sulfonic acid pretreatment group had symptoms of diarrhea. These results indicate that pantetheine-S-sulfonic acid has an effect of reducing the plasma lipid content and that of preventing the increase of plasma lipids superior to those of pantethine as well as an effect of alleviating side effects, particularly diarrhea. Thus, it has been proved that pantetheine-S-sulfonic acid is highly safe.

TEST 2

Male Wistar-Imamichi rats weighing about 160 g obtained from JCL Co., Ltd. were fed with type CE-2 diet (JCL Co., Ltd.) and water ad libitum for one week before the experiments were started. The rats were divided into 3 groups, i.e., a carbon tetrachloride-control group (liver trouble models), a pantethine treatment group and a calcium pantetheine-S-sulfonate treatment group. Each group comprised 20 rats. The rats were fed with the same foods as in the pretreatment period.

Pantethine and calcium pantetheine-S-sulfonate were dissolved in amounts of 400 mg and 544 mg in 1 ml of water and given at the doses of 1000 and 1361 mg/kg, respectively. Only water was given at a rate of 2.5 ml/kg to the carbon tetrachloride-control group. The pretreatment was effected by administering them orally for one week. Thereafter, 1 ml/kg of carbon tetrachloride was given by means of the intraperitoneal injection. 24, 48 and 72 hours before and after the injection, 5 rats were sacrificed each period by decapitation to determine glutamic oxaloacetic transaminase (GOT), glutamic pyruvic transaminase (GPT) and alkaline phosphatase in the serum as well as the serum and liver lipid peroxides.

The determination was effected by the following methods:
Glutamic oxaloacetic transaminase (GOT): Karmen method
Glutamic pyruvic transaminase (GPT): Karmen method.
Alkaline phosphatase: Kind King method
Serum and liver lipid peroxide: Yagi fluorescence method.

The results are shown in Tables 2 to 4.

TABLE 2

(1) GPT and GOT

| Group | Time after the treatment with carbon tetrachloride (h) | GPT (Karmen U/ml) | GOT (Karmen U/ml) |
|---|---|---|---|
| Carbon tetrachloride-control | 0 | 43.12 ± 7.26 | 60.55 ± 13.74 |
| | 24 | 325.83 ± 27.86 | 1171.21 ± 41.98 |
| | 48 | 155.33 ± 17.74 | 900.93 ± 35.14 |
| | 72 | 140.41 ± 12.24 | 794.77 ± 33.12 |
| Pantethine | 0 | 45.4 ± 7.14 | 65.83 ± 9.80 |
| | 24 | 236.26 ± 26.48* | 768.25 ± 7.36** |
| | 48 | 139.65 ± 21.56 | 745.15 ± 19.81 |
| | 72 | 64.33 ± 7.48** | 578.15 ± 100.1** |
| Calcium pantetheine-S-sulfonate | 0 | 36.6 ± 3.31 | 102.16 ± 8.66 |
| | 24 | 199.22 ± 48.4* | 855.78 ± 32.33** |
| | 48 | 189.61 ± 60.83 | 824.0 ± 15.3 |

TABLE 2-continued

(1) GPT and GOT

| Group | Time after the treatment with carbon tetrachloride (h) | GPT (Karmen U/ml) | GOT (Karmen U/ml) |
|---|---|---|---|
| | 72 | 91.99 ± 10.05* | 641.47 ± 87.46* |

Mean ± SE
*$p < 0.05$,
**$p < 0.01$
The significant difference is a difference from the carbon tetrachloride-control group determined at the same time.

It is apparent from Table 2 that calcium pantetheine-S-sulfonate significantly ($P < 0.05$) reduced the serum GPT 24 h after the administration of carbon tetrachloride, while the activity in the control group reached maximum at that time and that pantethine exhibited the similar inclination ($p < 0.05$). This fact indicates that the liver troubles are suppressed. 72 h after the administration of carbon tetrachloride, calcium pantetheine-S-sulfonate reduced GPT significantly ($p < 0.05$) to indicate that it accelerated the cure of the liver troubles.

As for serum GOT, it is understood from Table 2 that in the group to which calcium pantetheine-S-sulfonate was given, GOT was reduced significantly 24 h after the administration ($p < 0.01$) as compared with the control group and also 72 h after the administration ($p < 0.05$). This fact indicates that it suppress the initial stage of the liver troubles and accelerate the cure.

TABLE 3

(2) Serum and liver lipid peroxide

| Group | Time after the treatment with Carbon tetrachloride (h) | Serum lipid peroxide (nmols/ml) | Liver lipid peroxide (nmols/100 mg wet wt.) |
|---|---|---|---|
| Carbon tetrachloride-control | 0 | 1.72 ± 0.27 | 45.62 ± 7.06 |
| | 24 | 2.74 ± 0.27 | 537.74 ± 16.40 |
| | 48 | 3.32 ± 0.47 | 381.73 ± 3.54 |
| | 72 | 6.15 ± 0.53 | 96.32 ± 13.82 |
| Pantethine | 0 | 1.54 ± 0.16 | 58.84 ± 12.31 |
| | 24 | 3.84 ± 0.44 | 298.68 ± 10.57*** |
| | 48 | 3.74 ± 0.76 | 153.3 ± 3.62*** |
| | 72 | 6.13 ± 0.14 | 82.2 ± 6.95 |
| Calcium pantetheine-S—sulfonate | 0 | 1.6 ± 0.16 | 59.89 ± 14.22 |
| | 24 | 3.41 ± 0.65 | 227.27 ± 27.06*** |
| | 48 | 3.10 ± 0.25 | 134.2 ± 8.68*** |
| | 72 | 3.67 ± 0.59* | 72.36 ± 3.77 |

Mean ± SE
*$p < 0.05$
***$p < 0.001$
The significant difference is a difference from the carbon tetrachloride-control group determined at the same time.

TABLE 4

Alkaline Phosphatase

| Group | Time after the treatment with $CCl_4$ (h) | Alkaline phosphatase activity (K.A. Unit) |
|---|---|---|
| Carbon tetrachloride-control | 0 | 38.6 ± 1.8° |
| | 24 | 102.7 ± 3.4 |
| | 48 | 124.0 ± 3.3 |
| Pantethine | 0 | 37.0 ± 3.7 |
| | 24 | 45.9 ± 12.3*** |
| | 48 | 62.5 ± 28.6* |
| Calcium pantetheine-S—sulfonate | 0 | 39.3 ± 2.8 |
| | 24 | 39.8 ± 3.4*** |
| | 48 | 39.3 ± 5.1*** |

° Mean ± SE
*$p < 0.05$
***$p < 0.001$
The significant difference is a difference from the carbon tetrachloride-control group determined at the same time.

It is apparent from Table 3 that as compared with not only the control group but also the pantethine treatment group, serum lipid peroxide in the calcium pantetheine-S-sulfonate treatment group was reduced significantly ($p < 0.05$) 72 h after the administration. Thus, calcium pantetheine-S-sulfonate remarkably suppressed the formation of serum lipid peroxide.

It is also apparent from Table 3 that as compared with the control group, liver lipid peroxide in the calcium pantetheine-S-sulfonate treatment group was reduced significantly ($p < 0.001$) 24 h and 48 h after the administration. This fact indicates that calcium pantetheine-S-sulfonate remarkably inhibits the formation and storage of lipid peroxide in the liver.

It is apparent from Table 4 that the increase of alkaline phosphatase activity which is an enzymatic indication of cholangia was inhibited significantly 24 and 48 h after the treatment with carbon tetrachloride in the control group by the administration of calcium pantetheine-S-sulfonate and pantethine. The inhibition effect of calcium pantetheine-S-sulfonate was superior to that of pantethine. From the results, the effects of calcium pantetheine-S-sulfonate on cholangia were confirmed.

As described above with reference to calcium salt of pantetheine-S-sulfonic acid, it was proved that pantetheine-S-sulfonic acid and its salts have effects of inhibiting the formation of liver lipid peroxide in patients with liver troubles which effects are equivalent to those of pantethine which is an analogous drug and also effects of inhibiting the formation of serum lipid peroxide which effects are superior to those of pantethine in patients with cholangia. Thus, it was proved that pantetheine-S-sulfonic acid and its salts are quite useful as lipid metabolism improving drugs for patients with liver troubles.

TEST 3

Male Golden hamsters weighing about 120 g obtained from JCL Co., Ltd. were used. The hamsters were divided into 3 groups, i.e., a control group (normal models), a pantetheine-S-sulfonic acid treatment group and a pantethine treatment group. Each group comprised 4 hamsters. The hamsters were fed with commercially available solid type CE-2 diet (JCL Co., Ltd.) and city water ad libitum. As pantetheine-S-sulfonic acid ($PaSSO_3H$), its calcium salt was used in the form of a 544 mg/ml solution in water and pantethine (PaSS) was used in the form of a 400 mg/ml solution in water.

2.5 ml/kg of water was given orally to the hamsters of the control group. 1,361 mg/kg of pantetheine-S-sulfonic acid and 1,000 mg/kg of pantethine were given to the hamsters of the other two groups, respectively. The treatment was effected by the oral administration once a day at 11 A.M. for two weeks. 24 h after the completion of the treatment, blood was taken by decapitation and serum lipids were determined by conventional methods. The method of serum lipids determination were as shown below:

Cholesterol: Enzymic method (Cholesterol-C Test Wako),
Triglyceride: Chemical method (Triglyceride-G Test Wako),
Phospholipids: Enzymic method (Phospholipid-B Test Wako),
HDL-cholesterol: Heparin-manganese bonding precipitation method (HDL-cholesterol Test Wako),
$\beta$-Lipoprotein cholesterol: Enzymic method ($\beta$-Lipoprotein-C Test Wako).

The results are shown in Table 5.

TABLE 5

Effects of pantetheine-S—sulfonic acid on serum lipids in hamsters

| Group | Chol. (mg/dl) | TG (mg/dl) | HDL-Chol (mg/dl) | $\beta$-LP-Chol (mg/dl) |
|---|---|---|---|---|
| Control | 220.9 ± 9.3* | 314.8 ± 17.0 | 36.7 ± 2.0 | 167.4 ± 14.0 |
| $PaSSO_3H$-treatment | 150.4 ± 6.3 | 104.2 ± 6.3 | 98.5 ± 3.5 | 71.8 ± 3.5 |
|  | C: P < 0.001 | C: P < 0.001 | C: P < 0.001 | C: P < 0.001 |
| PaSS-treatment | 157.2 ± 8.5 | 150.5 ± 10.2 | 97.1 ± 7.1 | 74.2 ± 6.3 |
|  | C: P < 0.01 | C: P < 0.001 | C: P < 0.001 | C: P < 0.001 |

*Mean ± S.D.

C: Significant difference from the control group
Chol: Cholesterol
TG: Triglyceride
HDL-Chol: High density lipoprotein-cholesterol
$\beta$-LP-chol: $\beta$-Lipoprotein cholesterol (the sum of VLDL-cholesterol and LDL-cholesterol)
VLDL: Very low density lipoprotein
LDL: Low density lipoprotein It has been found in these experiments that hamsters are particularly suitable test animals for the study of the serum neutral fat. Namely, as compared with rats usually used for the experiments, hamsters have 2-fold total serum cholesterol and far higher triglyceride concentration. If hamsters are used, it becomes unnecessary to forcedly realize artificial hyperlipidemic conditions and also to realize an extremely unbalanced metabolism in rats by Triton injection or feeding them on hypercholesterolemic diets for examining the effects of drugs. In other words, if hamsters are used, the effects of drugs can be examined under considerably normal metabolism conditions of animals, namely, behaviors of drugs can be observed under nearly natural conditions advantageously. Further, the lipoprotein metabolism in rats is different from that in human bodies and the components per se of lipoprotein in rats are different from that in human bodies and, therefore, the application of the experimental data on rats to human bodies is unreasonable in the analysis of the data. In this connection, it has been said that the mechanism of the lipoprotein metabolism of hamsters is like that in human bodies. In addition, the components of lipoprotein in hamsters are very close to that in human bodies.

Thus, if hamsters are used in the experiments, physiological effects quite similar to those observed in human bodies are obtained. To put it strongly, the physiological effects obtained in hamsters can be directly applied to human bodies.

When pantetheine-S-sulfonic acid was given to hamsters which are animals quite suitable for the experiments according to the present invention for 2 weeks, serum cholesterol was reduced by about 32% (p<0.001) (when pantethine was given, the reduction was 29% and p<0.01) and triglyceride was reduced by 67% (p<0.001) (when pantethine was given, the reduction was 53% and p<0.001). It is thus understood that the effects of pantetheine-S-sulfonic acid were far superior to those of pantethine.

It has been said that $\beta$-lipoprotein-cholesterol is a risk factor for arteriosclerosis. Pantetheine-S-sulfonic acid reduced the $\beta$-lipoprotein-cholesterol significantly (p<0.001) as compared with the control group. Pantetheine-S-sulfonic acid exhibited the effects superior to those of pantethine.

HDL-cholesterol activates lecithin-cholesterol acyltransferase (LCAT) and acts as a catalyst in the esterification of free cholesterol to form an esterified cholesterol. Thus, HDL-cholesterol regulates smooth metabolism of cholesterol to prevent arteriosclerosis. HDL-cholesterol was increased significantly (p<0.001) in the pantetheine-S-sulfonic acid treatment group as compared with the control group. Thus, quite excellent results were obtained.

As described above, it has been found that pantetheine-S-sulfonic acid has remarkable lipid metabolism improving effects in all aspects of serum lipids and anti-arteriosclerotic activity.

The following examples will further illustrate the present invention.

EXAMPLE 1

500 mg of calcium pantetheine-S-sulfonate was stirred together with 5 g of powdery glucose. The mixture was distributed into vials under sterile conditions. The vials were sealed and stored at a dark, cool place after the introduction of nitrogen. At the time of use, 500 ml of 0.85% physiologic saline is added thereto to prepare a liquid drug. This liquid is used as an intravenous injection or drip depending on symptoms.

EXAMPLE 2

50 g of powdery glucose was added to 50 g of calcium pantetheine-S-sulfonate. 99 g of lactose, 1 g of hydroxypropylcellulose and 2 g of magnesium stearate were weighed and added to the mixture. The mixture was thoroughly stirred and shaped into tablets by means of a tableting machine to form 1000 tablets for adults.

EXAMPLE 3

100 g of calcium pantetheine-S-sulfonate, 730 g of lactose, 7 g of crystalline cellulose and 3 g of hydroxypropylcellulose were mixed together homogeneously. The mixture was shaped into granules through a screen of an extruder and dried sufficiently.

What is claimed is:

1. A method of improving lipid metabolism, comprising administering to an adult patient in need of lipid metabolism therapy pantetheine-S-sulfonic acid or a pharmaceutically acceptable salt thereof at a dosage rate of 100 to 10,000 mg/day.

2. A method of improving lipid metabolism according to claim 1, comprising administering to said adult patient a salt of pantetheine-S-sulfonic acid selected from the group consisting of an amine salt, pyridinium salt, alkali metal salt or alkaline earth metal salt at a dosage rate of 100 to 10,000 mg/day.

3. A method of improving lipid metabolism according to claim 2, comprising administering to an adult patient in need of therapy a salt of pantetheine-S-sulfonic acid selected from the group consisting of a pyridinium salt, a sodium salt, a potassium salt, a magnesium salt and a calcium salt at a dosage rate of 100 to 10,000 mg/day.

4. A method of improving lipid metabolism as in claim 1, wherein said dosage rate is 300 to 6,000 mg/day.

5. A method of improving lipid metabolism as in claim 2, wherein said dosage rate is 300 to 6,000 mg/day.

6. A method of improving lipid metabolism as in claim 3, wherein said dosage rate is 300 to 6,000 mg/day.

7. A method of lowering lipid peroxide concentrations in serum and in the liver, comprising administering to an adult patient in need of therapy to reduce lipid peroxide levels, pantetheine-S-sulfonic acid or a pharmaceutically acceptable salt thereof at a dosage rate of 300 to 6,000 mg/day.

8. A method of decreasing serum $\beta$-lipo-protein-cholesterol and increasing serum HDL-cholesterol in normolipidemic adult humans, comprising administering to a normolipidemic adult human pantetheine-S-sulfonic acid or a pharmaceutically acceptable salt thereof at a dosage rate of 100 to 10,000 mg/day.

9. A method of decreasing serum $\beta$-lipo-protein-cholesterol and increasing serum HDL-cholesterol in normolipidemic adult humans as in claim 8, wherein said dosage rate is 300 to 6,000 mg/day.

* * * * *